(12) United States Patent
Marechal et al.

(10) Patent No.: US 7,435,583 B2
(45) Date of Patent: Oct. 14, 2008

(54) MEMBRANE FRACTIONS OF 1,2-SN-DIACYLGLYCEROL-ENRICHED CELLS

(75) Inventors: Eric Marechal, Grenoble (FR); Stéphane Miras, Lancey (FR); Jacques Joyard, Meylan (FR)

(73) Assignees: Commissariat a l'Energie Atomique, Paris (FR); Centre National de la Recherche Scientifique, Paris (FR)

( * ) Notice: Subject to any disclaimer, the term of this patent is extended or adjusted under 35 U.S.C. 154(b) by 282 days.

(21) Appl. No.: 10/415,480

(22) PCT Filed: Oct. 26, 2001

(86) PCT No.: PCT/FR01/03329

§ 371 (c)(1),
(2), (4) Date: Apr. 30, 2003

(87) PCT Pub. No.: WO02/36811

PCT Pub. Date: May 10, 2002

(65) Prior Publication Data

US 2004/0013739 A1    Jan. 22, 2004

(30) Foreign Application Priority Data

Oct. 31, 2000  (FR) .................................. 00 13976

(51) Int. Cl.
*C12N 9/00*     (2006.01)
*C12N 5/68*     (2006.01)
*C12N 15/70*    (2006.01)
*C12N 15/82*    (2006.01)
*C07H 21/04*    (2006.01)

(52) U.S. Cl. .................. 435/317.1; 435/4; 435/7.2; 435/183; 435/69.1; 800/278; 536/23.2; 536/23.6

(58) Field of Classification Search .............. 435/15, 435/183, 23.2
See application file for complete search history.

(56) References Cited

FOREIGN PATENT DOCUMENTS

FR         2 790 915        9/2000

OTHER PUBLICATIONS

Hawi et al. Detection of membrane-bound enzymes in cells using immunoassay and Raman microspectroscopy, Anal Biochem. Jun. 1, 1998;259(2):212-7.*
Dorne et al., "Do Thylakoids Really Contain Phosphatidylcholine?" Proceedings of the National Academy of Sciences of the United States, vol. 87, No. 1, 1990, pp. 71-74.
Miège et al., "1,2-sn-Diacylglycerol in Plant Cells: Product, Substrate and Regulator," Plant Physiology and Biochemistry (Paris), vol. 37, No. 11, Nov. 1999, pp. 795-808.
Miège, C., "Caractérisation Moléculaire et Biochimique de la Monogalactosyl Diacylglycerol Synthase (MGDG Synthase) de l'enveloppe des chloroplastes d'épinard," Feb. 19, 1998, Université Joseph Fourier, Grenoble XP002178791, pp. 130.
Maréchal et al., "Kinetic Properties of Monogalactosyldiacylglycerol Snythase From Spinach Chloroplast Envelope Membranes," Journal of Biological Chemistry, American Society of Biological Chemists, vol. 269, No. 8, Feb. 25, 1994, pp. 5788-5798.
Shimojima et al., "Cloning of the Gene for Monogalactosyldiacylglycerol Synthase and its Evolutionary Origin," Proceedings of the National Academy of Sciences of USA, National Academy of Science, vol. 94, Jan. 1997, pp. 333-337.

* cited by examiner

*Primary Examiner*—Rebecca E. Prouty
*Assistant Examiner*—Iqbal H Chowdhury
(74) *Attorney, Agent, or Firm*—Morgan, Lewis & Bockius LLP

(57) ABSTRACT

The invention concerns membrane fractions of cells containing a recombinant MGDG synthase and enriched with 1,2-sn-diacylglycerol, their preparation method, their use for screening molecules inducing MGDG synthase activity and a method for screening molecules inducing MGDG synthase activity using said membrane fractions.

12 Claims, 3 Drawing Sheets

Slope: 340 nmol/h/mg

MEMBRANE FRACTIONS OF 1,2-SN-DIACYLGLYCEROL-ENRICHED CELLS

Figure 1:
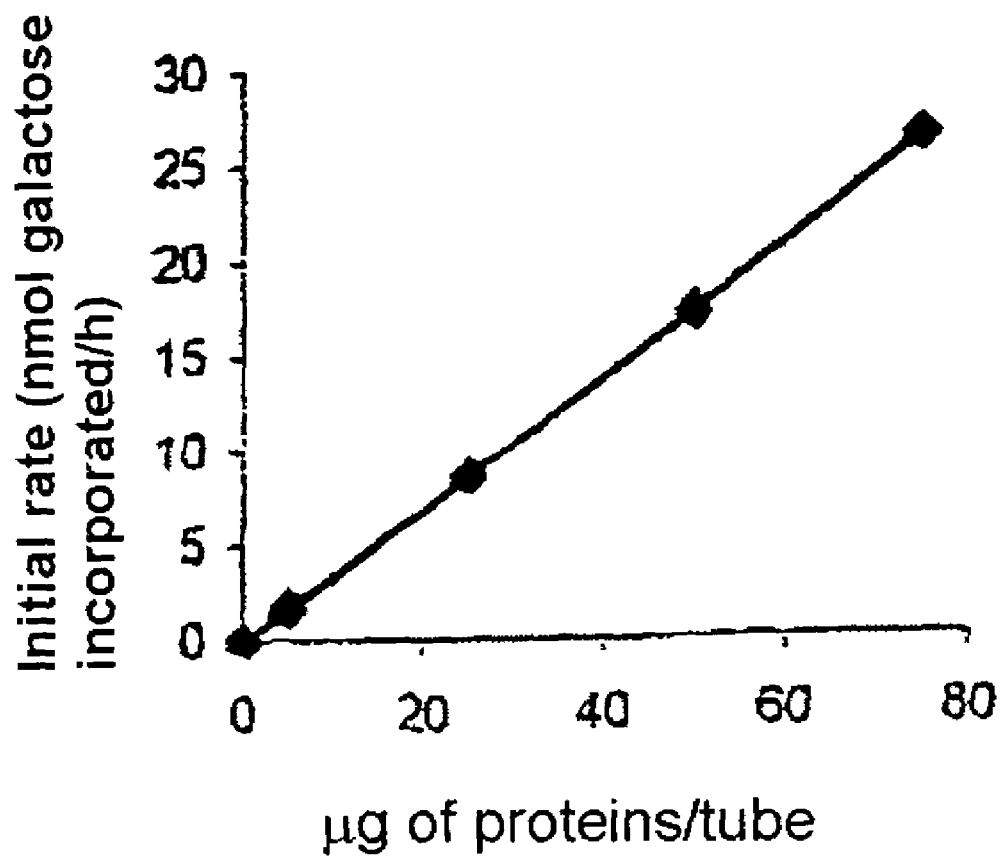

The present invention relates to membrane fractions of cells containing a recombinant monogalactosyldiacylglycerol (MGDG) synthase and enriched in 1,2-sn-diacylglycerol (DAG), to the method of preparing them, to their use for screening molecules having an effect on MGDG synthase activity and to a method of screening molecules having an effect on MGDG synthase activity, using these membrane fractions.

MGDG is known to be in all plasts analyzed to date: it is the most abundant lipid of plastid membranes, where it represents more than 50% of glycerolipids. MGDG is vital to plast biogenesis and to cell survival, and does not exist in the other membrane systems, in particular in animal cells (Douce, Sciences, 1974, 183, 852-853); the biosynthesis thereof is catalyzed in the envelope by a uridine 5'-diphosphate galactose (UDP-gal) 1,2-diacylglycerol 3-β-D-galactosyltransferase (EC 2.4.1.46) also called MGDG synthase, according to the following reaction:

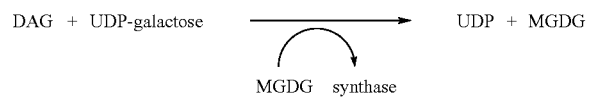

$$DAG + UDP\text{-galactose} \xrightarrow{MGDG\ synthase} UDP + MGDG$$

MGDG synthase is a bifunctional enzyme which binds substrates in a non-ordered manner (Maréchal et al., J. Biol. Chem, 1994, 269, 5788-5798), which has oxidation-sensitive cysteines and which is important for catalysis (Maréchal et al., J. Biol. Chem., 1995, 270, 11, 5714-5722).

MGDG synthase is therefore also an enzyme essential to plast biogenesis and is, consequently, a target of choice for selecting or screening molecules with herbicidal potential. In addition, the parasites responsible for malaria (4 species of *Plasmodium*, including *P. falciparum*), for toxoplasmosis (*Toxoplasma gondii*) and for scourges of the veterinary field, such as coccidiosis (*Eimeria*) contain degenerate chloroplasts (apicoplasts) which have been demonstrated to be essential to parasite survival (G. McFadden and David Roos, "Apicomplexan plastids as drug targets", 1999, 7, No. 8, 328-333).

The parasites which contain these apicoplasts are called apicomplexan parasites.

A molecule which has an inhibitory action on MGDG synthase activity therefore has a high herbicide and anti-apicomplexan parasite potential and can be used advantageously as a novel medicinal product effective against said apicomplexan parasites or as a herbicide.

The use of an MGDG synthase for selecting or screening products inhibiting MGDG synthase activity, able to be used as herbicides or as active principles against apicomplexan parasites has already been proposed, in particular in patent application FR-A-2 790 915.

According to that application, the selection and/or screening of such products is (are) carried out according to a method comprising incubating a test substance with an MGDG synthase embedded in biological membranes, and then measuring the specific enzyme activity, after said incubation.

The biological membranes used in that prior application can in particular be plastid membranes isolated from plants or else membrane fractions of *E. coli* overexpressing a recombinant MGDG synthase.

Measuring the galactosylation activity carried out by MGDG synthase is, at the current time, very complex and cannot be readily miniaturized, in particular for the following reasons:

(1) Addition of two substrates: The two substrates of the enzyme (DAG and UDP-gal) should be added simultaneously to the incubation medium. Homogeneity of the system is a problem, in particular due to the fact that these two substrates have very different physicochemical properties: one is very hydrophilic (UDP-gal), the other is very hydrophobic (DAG). The control of the introduction of these two substrates is therefore difficult to miniaturize.

(2) Addition of a detergent: DAG is so hydrophobic that it is not water-miscible. In order for the enzyme to have access to this exogenous substrate, a detergent therefore has to be introduced into the incubation medium, for example 3-[(3-cholamidopropyl)dimethylammonio]-1-propanesulfonate (CHAPS), which pulverizes the biological membranes and allows a rearrangement of all the hydrophobic molecules in the form of micelles. The micelles are too small to be separated from the reaction medium by filtration or centrifugation (Stoke's radius 3.8 nm; Maréchal et al, 1994, mentioned above).

(3) Phase separation: In order to extract the lipid phase containing the reaction product (MGDG), a mixture of organic solvents (chloroform and methanol) is added at the end of the reaction according to the method described by Bligh et al. (Can. J. Biochem. Physiol., 1959, 37, 911-917). A biphase forms and the lipids are recovered in the lower organic phase. The formation of a biphase and the extraction of an organic phase are processes which are too sophisticated to be used in a miniaturized process.

Now, in the context of the search for molecules having an effect on MGDG synthase activity, it is essential to have a simple, relatively inexpensive, rapid and miniaturizable method for testing a very large number of molecules potentially able to be used as herbicides or as active principles against apicomplexan parasites.

The inventors have developed the subject of the invention in order to remedy these problems.

Specifically, the inventors have developed new biological membrane fractions containing, in the same lipid leaflet, both MGDG synthase and DAG. These membranes can be used in an enzyme method for automated high throughput screening (HTS) of molecules having an effect on MGDG synthase activity (inhibitors or activators).

A subject of the present invention is therefore plasma membrane fractions from prokaryotic cells or eukaryotic animal cells, consisting of a lipid leaflet containing at least one recombinant MGDG synthase, characterized in that said fractions contain at least 1% by weight of DAG relative to the total weight of protein, and in that they are in the form of spherical vesicles.

The inventors have in fact demonstrated that the simultaneous presence of MGDG synthase and DAG in said membrane fractions makes it possible to use these membrane fractions in a method of screening and/or selecting molecules having an effect on MGDG synthase activity, in which the volumes of the reaction media can be considerably reduced, thus enabling miniaturization of said method.

By virtue of these membrane fractions, the addition of detergent to promote the control MGDG synthase/DAG mixing is eliminated, and the enzyme reaction takes place directly within the membranes.

According to a preferred embodiment of the invention, the MGDG synthase/DAG molar ratio is less than 10, and even more particularly less than 0.12.

Specifically, the enzyme/substrate ratio should respect the conditions for measurement making it possible to use the Michaëlis-Menten enzymological model; in particular, the substrate should not be the limiting factor of the initial reaction.

The membrane fractions in accordance with the invention are preferably in the form of spherical vesicles made up of a lipid bilayer.

These membrane vesicles are generally between 0.1 μm and 10 μm in size.

Within these vesicles, the MGDG synthase is, in general, located on the inner face of the lipid bilayer.

These vesicles may be in the form of noninverted, inverted or hybrid vesicles.

Disruption of the membranes in fact allows the formation of inverted or noninverted vesicles; but in both cases, the MGDG synthase is on the face opposite most of the DAG. Fusion between inverted and noninverted vesicles can generate a new family of vesicles having the MGDG synthase and the DAG in the same lipid leaflet.

This type of hybrid vesicle can exhibit increased catalytic activity (accessible substrate) and is, consequently, preferred according to the invention.

A subject of the invention is also a method of preparing membrane fractions as described above, characterized in that it consists:
- in a first step, in transforming prokaryotic cells or eukaryotic animal cells with a construct containing the gene encoding a plant MGDG synthase,
- in a second step, culturing said cells in a culture medium which promotes protein synthesis, so as to induce the synthesis of MGDG synthase by said cells,
- in a third step, in incubating the cells cultured in the preceding step in a reaction medium containing at least one phospholipase C,
- and then, in a fourth step, in fractionating the cells thus enriched in DAG so as to obtain membrane fractions in the form of spherical vesicles containing at least one recombinant MGDG synthase and at least 1% by weight of DAG relative to the total weight of proteins of said membrane fractions.

Among the prokaryotic cells which can be used according to this method, mention may be made of bacteria such as *E. coli*, which are particularly preferred according to the invention.

Among the eukaryotic cells which can be used according to this method, mention may be made of cells from yeast, such as *Saccharomyces cerevisiae*, cells from insects, such as drosophila, and also mammalian cells conventionally used to express genes, such as COS cells and CHO cells.

The transformation of the cells in the first step is preferably carried out on bacterial cells, and more particularly on *E. coli* cells.

This transformation can be carried out according to the method described in patent application FR-A-2 790 915, for example by heat shock, with a plasmid pET-Y3a containing the sequence encoding *Arabidopsis thaliana* MGDG synthase A (Miège et al., Eur. J. Biochem., 1999, 265, 990-1001).

The culture medium used in the second step is a rich culture medium, in order to promote expression of the MGDG synthase, and is chosen as a function of the type of cells to be cultured. In the particular case of bacterial cells, and in particular of *E. coli*, Luriat Broth (LB) medium can be used.

The use of PLC during the third step of the method of preparation in accordance with the invention is essential to the enrichment of the plasma cell membranes in DAG.

Specifically, these cell membranes are rich in phospholipids, particularly in phosphatidylethanolamine (80% of phospholipids). These phospholipids can be hydrolyzed by PLC, which is not specific for the polar head.

PLC catalyzes the conversion of phosphatidylethanolamine to DAG according to the following reaction:

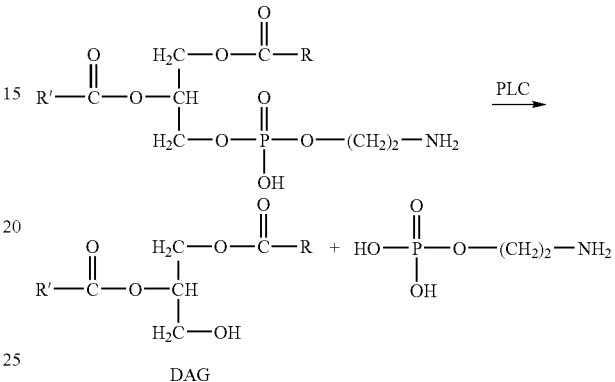

PLC therefore makes it possible to enrich the cell membranes in DAG by hydrolysis of its phospholipids.

The nature of the PLC used according to the invention is not critical, on condition that it is active on the phospholipids of the membranes intended to be enriched in DAG.

According to a particularly preferred embodiment of the invention, a *Bacillus cereus* phospholipase C is used.

The PLC is preferably used at a concentration between 1 U and 20 U per ml of reaction medium, and even more preferentially at a concentration between 5 and 12 U/ml.

Of course, the reaction medium used in the third step is generally a buffer medium the pH of which should be compatible with the correct functioning of the PLC. This pH is generally between 6 and 8.

In the fourth step, the membranes are fractionated so as to generate membrane fractions which close up spontaneously in the form of membrane vesicles. The fractionation of the membranes can be carried out by mechanical shock, for example using a French press, by thermal shock (freezing/thawing), or by osmotic, electric or else physical shock, such as by sonication.

The membrane fractions thus obtained can then optionally be purified, for example on a cushion of Percoll.

When the preparation of the membrane fractions in accordance with the invention is finished, they can optionally be frozen before being used for selecting or screening molecules having an effect on MGDG synthase activity.

A subject of the invention is therefore also the use of the membrane fractions as described above, for selecting and/or screening molecules having an effect on MGDG synthase activity.

In particular, a subject of the invention is the use of the membrane fractions as described above, for selecting or screening molecules inhibiting MGDG synthase activity, able to be used as active principles against parasites or as herbicides.

A subject of the invention is also a method of selecting and/or screening molecules having an effect on MGDG synthase activity, characterized in that it comprises:

a step comprising incubation of the test substance(s) with a sufficient amount of membrane fractions as defined above and of radiolabeled UDP-galactose in an aqueous phase having a pH of between 4 and 11, a step comprising washing of the membrane fractions, a step comprising separation of the membrane fractions, then a step comprising determination of the MGDG synthase activity.

According to this method, the enzyme reaction takes place directly within the membrane fractions, the size of which is compatible with separation from the reaction medium by centrifugation or by filtration. Using this means, it is no longer necessary to use organic solvent to extract the reaction products, the MGDG in fact being trapped in the membrane fractions on which a simple measurement of the radioactivity of the radiolabeled galactose incorporated can be carried out.

According to a preferred embodiment of the invention, the aqueous incubation phase contains a buffer and has a pH of between 6 and 8.

By way of example, the buffer may in particular be 3-(N-morpholino)propanesulfonic acid or a $KCl/K_2HPO_4$ mixture.

The amount of UDP-galactose to be used in the incubation medium should, of course, be sufficient so as not to constitute a limiting factor of the reaction. This amount is preferably between 0.1 and 10 nmol per µl of reaction medium.

The incubation step is preferably carried out at ambient temperature, for a period of at least 10 seconds, and even more particularly for a period of between 1 and 45 minutes.

At the end of the incubation step, the reaction is preferably stopped by cooling the incubation medium (in general to a temperature of approximately 4° C.) or by centrifugation.

When the reaction is finished, the step comprising washing of the membrane fractions is carried out in order to eliminate the excess radiolabeled UDP-galactose which has not been incorporated by the membrane fractions. One or more successive washes may be carried out, generally with water.

The membrane fractions are then separated by centrifugation or by filtration, the latter technique being particularly suitable for miniaturization of the method on microplates.

The determination of the MGDG synthase activity is carried out by measuring the amount of radiolabeled galactose incorporated into the membrane fractions. This measurement is conventionally carried out using a radioactivity counter.

The method of selecting and/or screening molecules having an effect on MGDG synthase activity in accordance with the invention can be readily miniaturized since it uses small reaction volumes and does not use detergents or organic solvent, as is the case in the methods previously described in the prior art.

A subject of the invention is also therefore microtitration plates comprising a multitude of wells, characterized in that the bottom of the wells consists of a filter and in that said wells contain membrane fractions as described above.

These microplates can be stored in a freezer before use. They can optionally be equipped with a detachable bottom.

The microplates in accordance with the invention make it possible to determine the MGDG synthase activity by direct measurement of the radioactivity of the radiolabeled galactose incorporated into the membrane fractions retained by the filter at the bottom of the wells.

They may therefore be used to test large "chimiotheques" [chemical libraries] of molecules for their activity of an effect on MGDG synthase activity.

Finally, a subject of the invention is the use of at least one molecule inhibiting MGDG synthase activity as selected in accordance with the method of screening and selecting in accordance with the invention, for preparing an antiparasitic medicinal product or a herbicide.

Figure 2A:
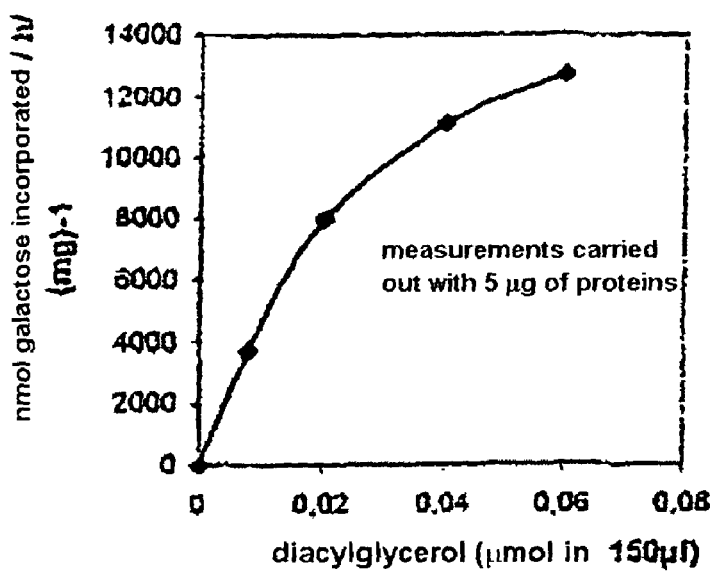
Figure 2B:
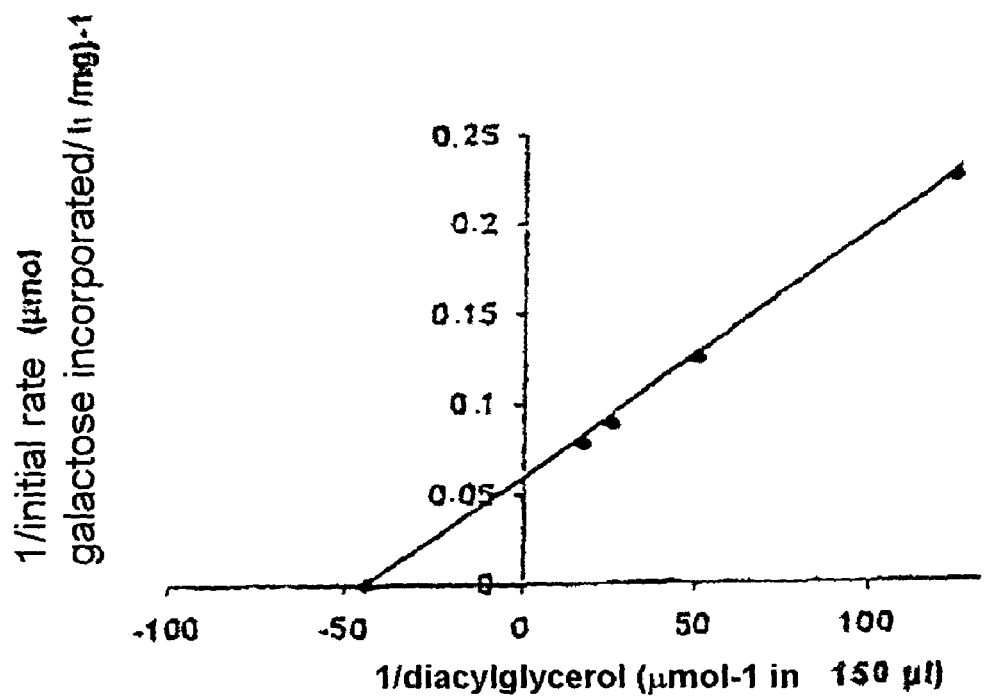
Figure 3:
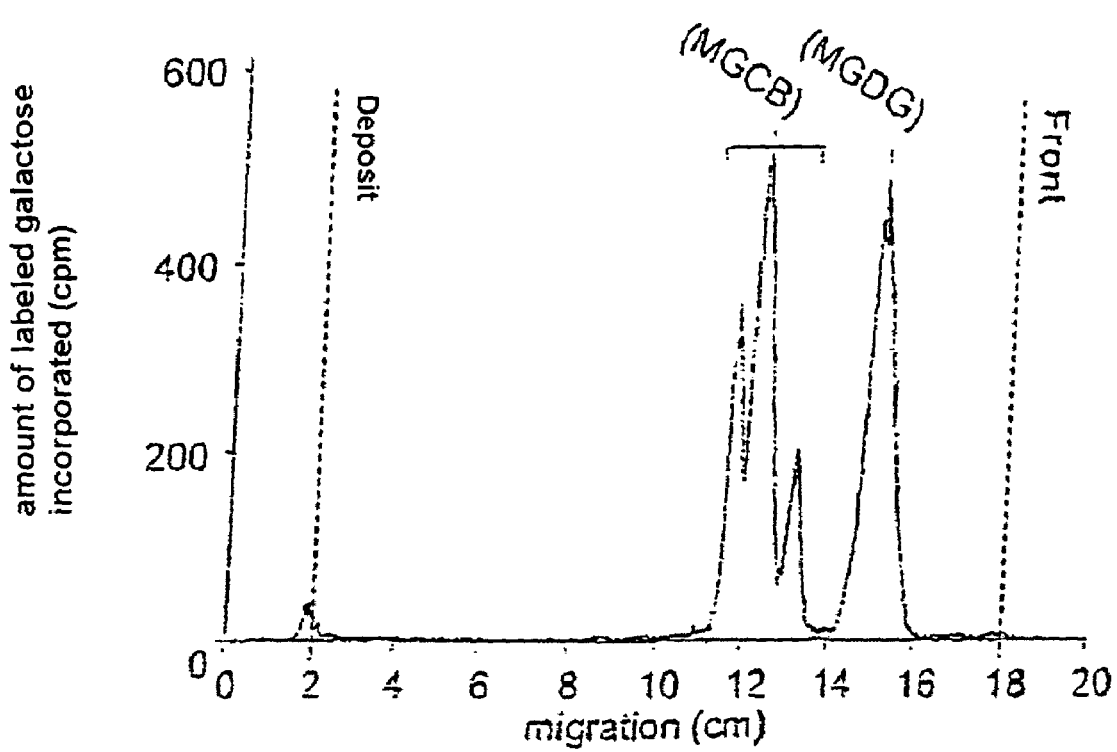

Besides the arrangements above, the invention also comprises other arrangements which will emerge from the following description, which refers to an example of preparation of membrane fractions in accordance with the invention, to a comparative example of determination of MGDG synthesis activity, to an example of demonstration of the presence of MGDG in an apicomplexan parasite, and to the attached figures, in which:

FIG. 1 represents the number of nmole of galactose incorporated per hour into membrane fractions enriched in DAG as a function of the number of µg of proteins, FIG. 2A represents the number of nmole of galactose incorporated per hour and per mg of proteins (membrane fractions enriched in DAG) as a function of the number of µmole of DAG, FIG. 2B represents an inverse coordinate plot of the Line Weaver and Burk type on which the inverse of the number of µmoles of galactose incorporated per hour and per mg of proteins is expressed as a function of the inverse of the number of µmoles of DAG;

FIG. 3 represents the amount of labeled galactose incorporated by the membrane lipids of *Toxoplasma gondii*.

It should be clearly understood, however, that these examples are given only by way of illustration of the subject of the invention, of which they in no way constitute a limitation.

EXAMPLE 1

Preparation of Membrane Fractions Containing an MGDG Synthase and DAG

1) Production of Recombinant MGDG Synthase in *E. coli*

A—Transformation of the Bacteria

The bacteria are transformed according to the method described in patent application FR-A-2 790 915.

All the cultures are prepared under sterile conditions. Competent bacteria (bacterial strain BL21 or BLR of *Escherichia coli*) are transformed by heat shock with a plasmid pET-Y3a which makes it possible to overcome the problem due to the fact that the deduced sequence of the MGDG synthase contains 22 arginine residues, among which 17 are encoded by AGG or AGA, codons which are in fact used very little in *E. coli*.

The plasmid pET-Y3a has been described in patent application FR-A-2 790 915 and is constructed by inserting the arg U gene (or DNA Y) encoding the arginine transfer RNA associated with the rare codons AGA/AGG, into the plasmid pET-3a (Novagen). The plasmid pET-Y3a contains the sequence encoding *Arabidopsis thaliana* MGDG synthase A (under the control of a promoter inducible with isopropyl-β-D-thiogalactopyranoside: IPTG), a carbenecillin resistance gene and a sequence encoding the arginine transfer RNA. This ARG4 tRNA allows the synthesis of proteins such as MGDG synthase, the sequence of which contains many Arg codons, which are rare in bacteria.

B—Production of Recombinant MGDG Synthase A in *E. coli*

A colony isolated from recombinant bacteria is transferred into 8 ml of Luria Broth (LB) medium in the presence of antibiotic (20 µg/ml final concentration of carbenecillin). The preculture is incubated at 37° C., with regular shaking, and the evolution of bacterial growth is followed by measuring the optical density (OD) at 600 nm, until a value of 0.5 is obtained.

The preculture is transferred into 500 ml of LB medium (20 µg/ml final concentration of carbenecillin) and incubated at 37° C. with regular shaking. At an OD measured at 600 nm of 0.5, the bacterial population is then in its exponential growth phase, which is a time of intense protein synthesis.

The addition of IPTG (0.4 mM final concentration) makes it possible to induce synthesis of the recombinant MGDG synthase.

The culture is then incubated for 3 hours with shaking at 28° C. in order to promote production of the protein in its active form.

The suspension of induced bacteria is divided up into two fractions of 250 ml and subjected to centrifugation for 15 minutes at 5 000 rpm (Sorvall® RCSC centrifuge, GS-3 rotor).

The recovered pellets are resuspended in 10 ml of culture medium (LB, carbenecillin at 20 µg/ml final concentration) and centrifuged for 15 minutes at 5 000 rpm (Sorvall® RCSC, SLA 600 TC rotor).

The supernatant is removed and the bacterial pellet is stored at −80° C.

2) Enrichment of the Bacterial Membranes in DAG by Treatment with Phospholipase C 5 ml of pellet of the bacteria induced for MGDG synthase in the previous step are resuspended in 5 ml of 10 mM 3-(N-morpholino)propanesulfonic acid (MOPS), pH 7.8, 1 mM dithiothreitol (DTT) and 10% (w/v)glycerol.

20 µl of *Bacillus cereus* phospholipase C (PLC) (phosphatidyl-choline cholinephosphohydrolase, EC 3.1.4.3) are added in order to obtain a final concentration of 8 U/ml. The reaction is carried out at ambient temperature for 3 hours with stirring and is stopped by adding EDTA (0.4 M final concentration).

3) Purification of Bacterial Membranes

A solution of the induced bacteria, the membranes of which are enriched in DAG by treatment with PLC, as obtained above in the previous step, is taken up in 50 ml of 5 mM MOPS, pH 7.8, 0.5 mM DTT, 5% (w/v)glycerol.

The bacteria are ruptured at high pressure (800 psi) using a French press: the membranes in aqueous solution then organize themselves spontaneously into vesicles and into inverted vesicles.

6 ml of the lysate obtained are deposited on a cushion of 35% Percoll (in 10 mM MOPS, pH 7.8, 1 mM DTT, 10% glycerol) and then centrifuged for 10 minutes at 5 000 rpm, at a temperature of 4° C. (Sorvall® RC SC, HB-6 rotor).

Vesicles consisting of a lipid bilayer containing MGDG synthase and at least 1% by weight of DAG relative to the total weight of protein are obtained.

Four fractions are then formed: a supernatant (in the upper part of the tube), the supernatant/Percoll interface, the cushion of 35% Percoll and a pellet.

All the membrane fractions are collected and washed by dilution with 5 volumes of 10 mM MOPS, pH 7.8, 1 mM DTT, 10% (w/v) glycerol, and centrifuged for 15 minutes at 5 000 rpm at a temperature of 4° C. (Sorvall® RCSC, HB-6 rotor).

The supernatants are removed and the pellets, which are fragile, are carefully taken up in 1 ml of washing medium so as to be centrifuged again for 10 minutes at 13 000 rpm at a temperature of 4° C. (Eppendorff centrifuge 5804).

The pellets are resuspended in 500 µl of 10 mM MOPS, pH 7.8, 1 mM DTT, 10% (w/v)glycerol and are stored at −20° C.

EXAMPLE 2

Comparative Determination of MGDG Synthesis Activity According to the Prior Art and According to the Invention I—Conventional Measurement of the MGDG Synthesis Activity According to the Method of Bligh and Dyer (1959)

This method was described in the article by Bligh and Dyer, "*A Rapid Method Of Total Lipid Extraction and Purification*", Can. J. Biochem. Physiol., 1959, 37, 911-917.

The measurement of the galactosylation activity is based on incorporation of the galactose originating from the radioactive ($^{14}$C) UDP-gal into the lipid fraction of the reaction medium.

The reaction is carried out at ambient temperature. 100 µg of DAG hydrophobic substrate (1 mg/ml) and 200 µg of phosphatidylglycerol (PG) in solution in chloroform (10 mg/ml) are introduced into a tube, dried under argon and then resuspended with 11 µl of a detersive medium (85 mM CHAPS, 0.7 M MOPS, 14 mM DTT), 75 µl of KCl (1 M) and 75 µl of KH$_2$PO$_4$ (1 M).

The presence of the detergent, in this case CHAPS, makes it possible to create mixed micelles containing the detergent, the DAG, the PG and the MGDG synthase originating from the sample.

After addition of 150 µl of sample, the final composition of the reaction medium (50 mM MOPS, 1 mM DTT, 250 mM KCl, 250 mM KH$_2$PO$_4$, 6 mM CHAPS in 300 µl of final volume) satisfies the criteria of the surface dilution model (Maréchal et al, 1995 mentioned above).

This example uses CHAPS as detergent, but it is also possible to use other detergents such as, for example, cholate, deoxycholate, Triton-X100®, NONIDET®, octylglucoside or lauryldimethylamine oxide (LDAO).

The reaction is started by introducing 10 µl of UDP-[$^{14}$C]-galactose (New England Nuclear 25 Bq/µmol, 10 mM). The reaction is stopped by adding 1.5 ml of a ½ (v/v) chloroform/methanol mixture.

The addition of 0.5 ml of chloroform and of 0.6 ml of water makes it possible, after centrifugation for 10 minutes at 1 000 rpm (Eppendorff A-4-44 centrifuge, 5804 rotor), to obtain a distinct biphase (a highly radioactive aqueous phase in the upper part of the tube, and an organic phase in the lower part).

The aqueous phase contains the radioactivity of the residual UDP-gal not used by the enzyme, while the organic phase contains the radioactivity of the hydrophobic product of the reaction: the MGDG.

After two washes of the aqueous phase with an identical volume of aqueous phase without UDP-[$^{14}$C]-gal, the organic phase containing the MGDG produced is transferred into a counting vial.

The fraction recovered is dried under argon and taken up in 10 ml of scintillation fluid, and the radioactivity of the sample is estimated.

The galactosylation activity is defined by the number of µmol of galactose incorporated into the lipid fraction per mg of protein and per hour.

II—Measurement by Purification of the Membranes after Centrifugation in Accordance with the Invention This measurement can be carried out only for a sample consisting of vesicles of membranes sequestering both the enzyme (MGDG synthase) and its hydrophobic substrate (DAG). Then only in this case, it is no longer necessary to add a detergent so that enzyme and substrate come into contact.

The reaction medium used is different from that given in the conventional method after extraction of the lipids with organic solvents.

The membrane fraction sample containing the MGDG synthase and the DAG, as obtained above in example 1, step 3, is suspended in a final volume of 300 µl containing 250 mM KCl and 250 mM $KH_2PO_4$.

The reaction is started by adding UDP-radiolabeled [$^{14}$C] gal.

The reaction is stopped by transferring to ice for 10 minutes.

Washing of the excess UDP-[$^{14}$C]gal (not incorporated into the membranes) is carried out by centrifugation of the sample for 10 minutes at 13 000 rpm at a temperature of 4° C., and taking up the pellet in 500 µl of sterile water.

This washing step is repeated three times. The pellet obtained is dried by centrifugation under vacuum for 1 hour (Eppendorff Concentrator 5301 Speed-vac). The dry sample is then taken up in a ½ (v/v) chloroform/methanol mixture, in order to transfer it into a counting vial, dried under argon, and solubilized with 10 ml of scintillation fluid.

The radioactivity of the sample is estimated using a Kontron® (Betamatic) counter.

The galactosylation activity is defined by the number of µmole of galactose incorporated per mg of protein and per hour.

III—Polyacrylamide Gel Electrophoresis Under Denaturing Conditions

The samples to be analyzed are suspended in the loading medium (0.15 M Tris HCl, pH 6.8, 10% glycerol, 0.02% SDS, 0.01% bromophenol blue, 0.025% DTT), and are then boiled for 4 minutes.

The acrylamide solutions are prepared in a 25 mM Tris buffer (pH 8.3 in the separating gel and pH 6.5 in the stacking gel) containing 0.192 M glycine and 0.1% sodium dodecyl sulfate (SDS).

The electrophoresis on a stacking gel (5% acrylamide) and then on a separating gel (12% acrylamide) is carried out at ambient temperature in a 25 mM Tris buffer containing 0.192 M glycine (pH 8.3) and 0.1% (w/v) SDS (U.K. Laemmli, Nature, 1970, 227, 680-683), under a constant voltage of 100 V.

The migration is stopped when the bromophenol blue leaves the gel.

The proteins are then stained with Coomassie blue (0.5% (w/v) Coomassie brilliant blue 8250, 25% methanol, 10% (v/v) acetic acid).

The gel is destained with successive baths of 25% isopropanol, 10% (v/v) acetic acid.

IV—Assaying of Proteins

Principle: the proteins are assayed by the Lowry method (Lowry et al., J. Biol. Chem., 1951, 193, 265-275), by measuring two simultaneous colored reactions.

A first reaction similar to the "biuret" reaction leads to the formation of a complex between the peptide bonds of the proteins (—CO—NH—) and the $Cu^{2+}$ ions in alkaline medium, and a second reaction leads to reduction of the Folin-ciocalteu reagent by the phenols of the tyrosines. This method makes it possible to assay solutions having a concentration ranging from 2 to 200 mg/ml.

Experimental approach: the volume of the sample to be assayed is adjusted to 200 µl with sterile water then 1 ml of assay reagent prepared extemporaneously (50 volumes of 2% $CO_3Na_2$, 0.1 N NaOH+1 volume of $CuSO_4$, 0.5% $SH_2O$, 1% sodium tartrate).

After reaction for 10 minutes at 20° C., 100 µl of Folin-ciocalteu reagent are added and the reaction is incubated at 20° C. for 30 minutes.

The amount of proteins in the sample to be assayed is determined by comparison of absorbence at 750 nm with a standard range established with bovine serum albumin (BSA).

V—Results

A—The Recombinant Bacteria must be Artificially Enriched in DAG in Order to Allow Measurement of the Galactosylation Activity in the Presence of UDP-Gal Analysis of the total proteins of bacterial samples taken during the induction step (example 1, step 1, FIG. 1) shows that induction with IPTG leads to an accumulation of MGDG synthase A representing approximately 30% of the proteins.

A comparison of the galactosylation activity measured in a crude extract of induced bacteria expressing the MGDG synthase A in the presence and in the absence of DAG was carried out.

The galactosylation activity was measured by extraction of the lipids according to the method of Bligh and Dyer (see above) on 20 µl of a bacterial culture induced at 28° C., in the absence of PG and possibly placed in the presence of 50 µg of DAG.

The results obtained appear in table I below:

TABLE I

| Incubation of bacteria in 270 µM of DAG | MGDG synthase activity (in nmole of galactose incorporated per hour) |
|---|---|
| yes | 576 |
| no | 5 |

These results show that a considerable galactosylation activity is observed in this extract incubated with 270 µM of DAG, whereas there is virtually no incorporation of galactose into the bacterial membranes incubated without the exogenous introduction of DAG.

Consequently, the bacterial membranes do not have a sufficient amount of endogenous DAG to carry out an isolated measurement of the activity of the recombinant enzyme.

B—Treatment of the Bacterial Membranes with PLC Generates DAG Available for Measuring Galactosylation Activity The galactosylation activity of the MGDG synthase was measured after synthesis of endogenous DAG by PLC or after addition of exogenous DAG. This activity was measured on 20 µl of the same bacterial culture induced at 28° C., in the presence or absence of 3 µl of PLC (2 000 U/ml), of 50 µg of DAG (at 1 mg/ml and optionally in the presence of 1 or 10 µl of $CaCl_2$.

The results are given in table II below:

TABLE II

| DAG in µM | PLC | $CaCl_2$ in µM | Galactose incorporated (nmol/hour) |
|---|---|---|---|
| — | — | — | 7 |
| 270 | — | — | 30 |
| — | + | — | 91 |
| 270 | + | — | 99 |
| 270 | + | 33 | 118 |
| 270 | + | 330 | 109 |
| — | + | 33 | 94 |
| — | + | 330 | 97 |

These results show that treating the bacterial membranes with PLC makes it possible to measure a galactosylation activity greater than that obtained after adding 270 μM of exogenous DAG.

The PLC therefore makes it possible to load the bacterial membranes with DAG by hydrolysis of its phospholipids. The poor incorporation of galactose obtained when adding DAG is explained by the fact that a very small proportion of added DAG was able to penetrate into the bacterial membranes in the absence of PLC, in order to act as substrate for the MGDG synthase.

It is also important to note that the calcium, which is an activator of PLCs, has no effect on the measured galactose incorporation, suggesting that the concentration of $Ca^{2+}$ of the bacterial suspension is sufficient to measure optimal activity of the PLC.

C—Incorporation of Radioactive Galactose into Membranes Enriched in DAG

The incorporation of radioactive galactose into the lysed membrane vesicles as described above in example 1, step B-3) was measured and compared to the incorporation of radioactive galactose by bacteria induced to express MGDG synthase A, but not lysed. The galactosylation activity is measured on 150 μl of sample (as described previously) in the presence or in the absence of 150 μg of PG (at 10 mg/ml) and of 100 μg of exogenous DAG (at 1 mg/ml).

The results obtained are given in table III below:

TABLE III

| | Galactose incorporated (nmol/hour) | |
|---|---|---|
| Induced bacteria, treated with PLC | Without exogenous introduction of DAG | +550 μM of exogenous DAG and 667 μM of PG |
| Not lysed | 2 426 | 6 622 |
| Lysed | 3 172 | 8 663 |

These results show that the galactosylation activity measured on lysed bacteria without the addition of DAG or PG indicates that vesicles containing both the MGDG synthase and the DAG have been formed, and that the enzyme has conserved its catalytic capacity.

They also show that the activity of the lysed fractions is greater than that of the non lysed fractions. This observation is coherent with the MGDG synthase A being located on the inner face of the lipid bilayer of the bacterial membranes. Specifically, since the PLC only has access to the outer lipid bilayer, the fraction of MGDG synthase located on the inner face can capture only a portion of the DAGs formed which have undergone transverse displacement from the outer leaflet to the inner leaflet of the membrane. The disruption of the membranes allows the formation of inverted and noninverted vesicles, but, in both cases, the MGDG synthase is on the face opposite most of the DAG. Fusion between inverted and noninverted vesicles may generate a new family of vesicles having, in the same membrane leaflet, the enzyme and the DAG. This type of vesicle may exhibit increased catalytic activity (accessible substrate). If it is supposed that the generation of these three populations of vesicles, inverted, non-inverted and hybrid, is equally probable, then the activity of the lysed samples is increased by a factor of 1.33 compared to the non lysed samples, which is observed in the present case.

D—Development of an Assay which can be Miniaturized

1) Demonstration of the Role of PLC

A suspension of lysed bacteria containing membrane vesicles enriched in MGDG synthase A and optionally in DAG by treatment with PLC is fractionated on a gradient of 35% Percoll (9 ml) as previously described. The fractions corresponding to the supernatant and to the interface (S+SL: 6 ml) and also those corresponding to the pellet (P: 1 ml) are collected. The galactosylation activity and the amounts of proteins are measured on the various fractions sampled (S+SL=6 ml, P=1 ml) and also of the fraction deposited (D of 6 ml).

The results obtained are given in table IV below:

TABLE IV

| Fractions | | Proteins in μg/ml | Total activity (in nmol UDP-gal incorporated/ hour) | Specific activity (nmol UDP-gal incorporated/ hour/mg) | Enrichment |
|---|---|---|---|---|---|
| No treatment with PLC | D | 400 | 103 | 43 | 1 |
| | S + SL | 136 | 363 | 445 | 10.3 |
| | P | 39 | 3 | 83 | 1.9 |
| Treatment with PLC | D | 500 | 618 | 206 | 1 |
| | S + SL | 880 | 11 462 | 2 169 | 10.5 |
| | P | 70 | 67 | 955 | 4.6 |

These results show that the membranes which have undergone enrichment in DAG by treatment with PLC are capable of converting much more UDP-gal than the membranes not enriched in DAG, since they have not undergone any treatment with PLC.

Analysis of the fractions by acrylamide gel electrophoresis under denaturing conditions shows enrichment for a polypeptide corresponding to MGDG synthase, from the supernatant to the pellet. The low galactosylation activity in the pellet (table IV) suggests an enrichment of this fraction mainly in inclusion bodies (inactive enzyme). The S+SL fractions containing the MGDG synthase A associated with the membranes enriched in DAG were therefore selected in order to analyze the enzyme activity of the MGDG synthase as a function of the criteria for validity of Michaelis-Menton enzymology.

2) Analysis of the Enzyme Activity of the MGDG Synthase

The results are given in FIG. 1, which represents the initial rate (in nmol of galactose incorporated per hour) as a function of the number of μg of proteins/tube. The initial rates were determined by measuring the incorporation of galactose after 15 and 30 minutes incubation of various amounts of the membranes treated with PLC and present in the treated S+SL fractions (25, 50, 75 μg of proteins).

This FIG. 1 shows that the incorporation of galactose is a linear function of the amount of sample incubated in the presence of UDP-gal. The slope of the curve makes it possible to deduce an activity of 340 nmol of galactose incorporated per hour and per mg of proteins.

The amount of DAG obtained after treatment with PLC is undetermined but the concentration of this substrate in the membrane vesicles remains constant whatever the amount of proteins of the sample. In this respect, the surface concentration of DAG (in molar fraction or in mol of DAG per unit of membrane surface) and the molar concentration of UDP-gal are constant. As a result, the initial reaction rate is directly proportional to the amount of proteins, showing the limiting nature of the amount of enzyme. The relationship of linearity is a condition of validation of conditions for Michaelis-Menton enzymological analysis.

3) Evaluation of the Amount of DAG Generated in the Bacterial Membranes by Treatment with PLC The activity (in number of nmol of galactose incorporated/hour/mg) of 5 μg of membranes not treated with PLC and purified on a Percoll gradient was measured for varying amounts of DAG introduced (FIG. 2A). The initial rates were determined by measuring the incorporation of galactose after 15 and 30 minutes of incubation. The measurements were made for varying amounts of DAG introduced (12.5 μg; 25 μg; 37.5 μg; per 300 μl of reaction medium).

The measurements make it possible to establish an inverted coordinate plot of the Lineweaver and Burk type (FIG. 2B).

If it is considered that the measurements made on membranes not treated with PLC constitute standard curves to estimate a DAG content, a sample of 5 μg, the intrinsic activity of which is 340 nmol/h/mg, is equivalent to the same untreated sample to which 0.5 μg of DAG has been added.

It is therefore possible to deduce therefrom that the treatment with PLC makes it possible to obtain about 0.1 μg of DAG per μg of proteins.

4) Measurement of the Galactosylation Activity of Membranes Enriched in MGDG Synthase and in DAG before and after Thawing The ability of membranes having undergone freezing for one day at −20° C. to incorporate galactose was measured and compared to that of membranes which had not undergone any freezing step.

No significant difference was observed between the two samples.

Consequently, this property makes it possible to prepare the sample of membranes and to manipulate it reproducibly in an automated device for screening molecules having an effect on MGDG synthase activity, which may comprise steps consisting of storing the sample under cold conditions, without loss of activity.

5) Simplified Measurement of the Galactosylation Activity Contained in the Sample of Membranes Enriched in MGDG Synthase and in DAG Membrane vesicles containing MGDG synthase enriched in DAG by treatment with phospholipase C, and optionally purified, can therefore be used to measure the production of MGDG in these same vesicles.

50 μg of membrane vesicles (equivalent to 50 μg of MGDG synthase and 50 μg of DAG) are suspended in an aqueous phase (250 mM KCl, 250 mM $K_2HPO_4$, 300 μl final volume, pH 7.8) contained in a tube (tube No. 1).

By way of comparison, a control tube (tube No. 2) was prepared: 50 μg of MGDG synthase and 50 μg of DAG were suspended in the same aqueous phase as that used in tube No. 1.

The reaction is initiated in each tube by adding 10 μl of UDP-gal radiolabeled with $^{14}C$ on the galactose, and then stopped after 30 minutes by cooling to 4° C.

The reaction medium of tube No. 1 is then centrifuged at 13 000 rpm for 10 minutes, rinsed several times with 500 μl of water, then centrifuged again at 13 000 rpm for 10 minutes.

Tube No. 2 was treated using the conventional method of lipid extraction with organic solvents, as described previously.

The radioactivity recovered in the centrifugation pellet (tube No. 1) was measured using a radioactive counter and was 4 026 dpm.

The radioactivity measured after extraction of the lipids in tube No. 2 was measured in the same way and was 4 136 dpm.

Consequently, the radioactivity measured for each of the tubes is not significantly different and makes it possible to validate the method of measuring the MGDG synthase activity in accordance with the invention.

The sample of membrane vesicles prepared in accordance with the invention contains the enzyme and its hydrophobic cosubstrate under conditions which correspond to measurement of the enzymological activity by the Michaelis method. In addition, this sample allows simple and miniaturizable measurement of the galactosylation activity by centrifugation and, by extension, by filtration.

VI—Conclusion

This example demonstrates that it is possible to use membrane fractions derived from a culture of cells expressing a recombinant MGDG synthase to measure a galactosylation activity respecting Michaelis-Menton laws, and the procedure for the measurement of which can be miniaturized on microplates.

It has also been demonstrated that the incorporated radioactivity can be simply recovered in the aggregates of the reaction medium, collected by centrifugation. Thus, the MGDG generated by this system accumulates in the membranes that a system of measurement by microfiltration is sufficient to measure, making it possible to use this enzyme assay for high throughput screenings (HTS) of active molecules. In particular, it is now possible to screen a "chimiothèque" [chemical library] by this method in order to select novel molecules with herbicidal potential. The inhibitors specific for MGDG synthase A thus produced will, moreover, be powerful pharmacological tools for allowing physiological studies of galactolipid synthesis.

EXAMPLE 3

Demonstration of MGDG Synthesis in an Apicomplexan Parasite

The aim of this example is to demonstrate the presence of MGDG in an apicomplexan parasite, *Toxoplasma gondii* and that, consequently, the MGDG synthase which serves as a target to search for a molecule with antiparasitic properties clearly exists in apicomplexans.

$2 \times 10^8$ cells of *Toxoplasma gondii*, in the form of tachyzoites, are suspended in 0.1 ml of a 1:10 mixture of 10 mM 3-(N-morpholino)propanesulfonic acid (MOPS), pH 7.8 and 1 mM dithiothreitol (DTT), containing 2% (w/v) glycerol and 50 mM of KCl, and then incubated for 30 min in the presence of 4 μCi of UDP-[$^3$H]-galactose (7.5 nmol).

The glycolipids are extracted according to the method of Bligh and Dyer, 1959 (mentioned above), then analyzed by thin layer chromatography (TLC) on 60μ silica gel plates resolved with a 65/25/4 (v/v) chloroform/methanol/water mixture, in the presence of control lipids (MGDG; bovine brain monogalactosyl cerebroside (MGCB); digalactosyldiacylglycerol (DGDG); trigalactosyldiacylglycerol (triGDG) and tetragalactosyldiacylglycerol (tetraGDG)).

The radioactivity of the labeled lipid is then detected using a TLC-analyzer device (LB2842 automatic TLC scanner).

The results obtained are given in FIG. 3, which illustrates the amount of labeled galactose (cpm) incorporated by the *Toxoplasma gondii* cells as a function of migration in centimeters.

On this figure, it is possible to see 3 first peaks which migrate to the same degree as the MGCB, whereas the last peak migrates to the same degree as the MGDG.

After migration, the lipids are visualized by spraying, onto the silica gel plates, a solution comprising 0.2% of orcinol and 75% of sulfuric acid, and then heating at a temperature of 100° C. for 15 minutes (results not given).

The peak corresponding to the MGDG disappears after alkali hydrolysis for 3 hours with 0.1 N potassium hydroxide in a water/methanol mixture.

Complete identification of the lipids is carried out after hydrolysis of the polar head with α-galactosidase from green coffee beans and β-galactosidase from bovine testes, and deacylation by alkali hydrolysis under gentle conditions (0.1 N KOH in a water/ethanol mixture for 3 hours).

Peak 4 is sensitive to hydrolysis with β-galactosidase, which shows that the galactose is clearly linked in the beta position, as for MGDG.

Moreover, after alkali hydrolysis, peak 4 disappears, which demonstrates that the lipid present in the *Toxoplasma gondii* membrane clearly contains half diacylglycerol.

This experiment demonstrates the existence of MGDG in the membrane of *Toxoplasma gondii* tachyzoites and confirms that an application of the search for inhibitors of plant MGDG synthase is the identification of anti-apicomplexan parasite agents.

The invention claimed is:

1. A bacterial plasma membrane fraction comprising a lipid leaflet containing a recombinant plant monogalactosyldiacylglycerol (MGDG) synthase from *Arabidopsis thaliana*, wherein said fraction contains at least 1% by weight of diacylglycerol (DAG) relative to the total weight of protein, and further wherein said fraction comprises spherical vesicles, the membrane of said spherical vesicles comprising a lipid bilayer.

2. The fraction as claimed in claim 1, wherein the MGDG synthase/DAG molar ratio is less than 10.

3. The fraction as claimed in claim 1, wherein the MGDG synthase/DAG molar ratio is less than 0.12.

4. The fraction as claimed in claim 1, wherein the membrane vesicles are between 0.1 μm and 10 μm in size.

5. The fraction as claimed in claim 1, wherein the MGDG synthase is located on the inner face of the lipid bilayer.

6. The fraction as claimed in claim 1, wherein the vesicles are in the form of noninverted, inverted or hybrid vesicles.

7. The fraction as claimed in claim 6, wherein the vesicles are in the form of hybrid vesicles comprising the MGDG synthase and the DAG in the same lipid leaflet.

8. A method of preparing the bacterial plasma membrane fraction as defined in claim 1, comprising:
   in a first step, transforming bacteria with a construct containing the gene encoding the recombinant plant MGDG synthase, wherein said plant is *Arabidopsis thaliana*
   in a second step, culturing said bacteria in a culture medium which promotes protein synthesis, so as to induce the synthesis of the recombinant plant MGDG synthase by said bacteria,
   in a third step, incubating the bacteria cultured in the preceding step in a reaction medium containing phospholipase C, and
   in a fourth step, fractionating the bacteria so as to obtain the plasma membrane fraction comprising spherical vesicles containing said recombinant plant MGDG synthase and at least 1% by weight of DAG relative to the total weight of protein of said membrane fraction.

9. The method as claimed in claim 8, wherein a *Bacillus cereus* phospholipase C is used.

10. The method as claimed in claim 8, wherein the phospholipase C is used at a concentration between 1 U and 20 U per ml of reaction medium.

11. The method as claimed in claim 8, wherein the fractionation of the membranes is carried out by mechanical shock, thermal shock, osmotic shock, electric shock or by physical shock.

12. Microtitration plates comprising a multitude of wells, wherein the bottom of the wells consists of a filter and further wherein said wells contain a membrane fraction as defined in claim 1.

* * * * *